(12) United States Patent
Bandeian, Jr. et al.

(10) Patent No.: US 6,445,304 B1
(45) Date of Patent: Sep. 3, 2002

(54) MEDICAL ALARM SYSTEM

(76) Inventors: John J. Bandeian, Jr.; John J. Bandeian, III, both of 3169 W. State St., Bristol, TN (US) 37620

( * ) Notice: Subject to any disclaimer, the term of this patent is extended or adjusted under 35 U.S.C. 154(b) by 0 days.

(21) Appl. No.: 09/636,376

(22) Filed: Aug. 11, 2000

(51) Int. Cl.$^7$ ............................................. G08B 21/00
(52) U.S. Cl. ...................... 340/604; 340/605; 600/371
(58) Field of Search .................. 340/604; 128/638; 304/605; 600/307, 371, 547

(56) References Cited

U.S. PATENT DOCUMENTS 4,193,068 A * 3/1980 Ziccardi ................... 340/604
5,579,765 A * 12/1996 Cox et al. .................. 128/638

* cited by examiner

*Primary Examiner*—Edward Lefkowitz

(57) ABSTRACT

A monitoring and alarm system for detecting excessive bleeding from medical patients and for alerting medical attendant(s) thereof, the system comprises a relatively thick sheet-like base of electrically non-conductive, blood porous material having a proximal side adapted for mounting directly on a patients skin or on a porous protective gauze or bandage or the like thereon at a site on the patients body where heavy bleeding can occur due to inadvertent opening of a wound or incision, or due to inadvertent extraction of a syringe, I.V. tube, catheter or the like, the base has a distal side, a normally open electrical circuit positioned adjacent the distal side and spaced from the proximal side a predesigned distance, electrically actuable visual, sound or physical alarm electrically connected into the circuit, and electrical switching for the circuit responsive to contact with blood to close the circuit and actuate the alarm to alert the medical attendant(s) to the excessive bleeding.

16 Claims, 1 Drawing Sheet

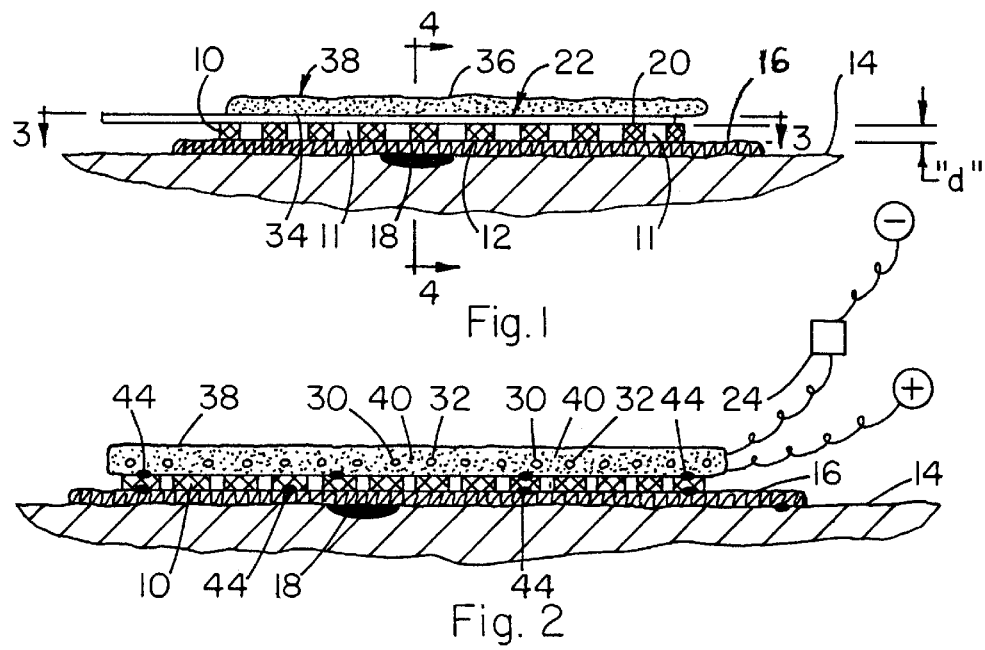
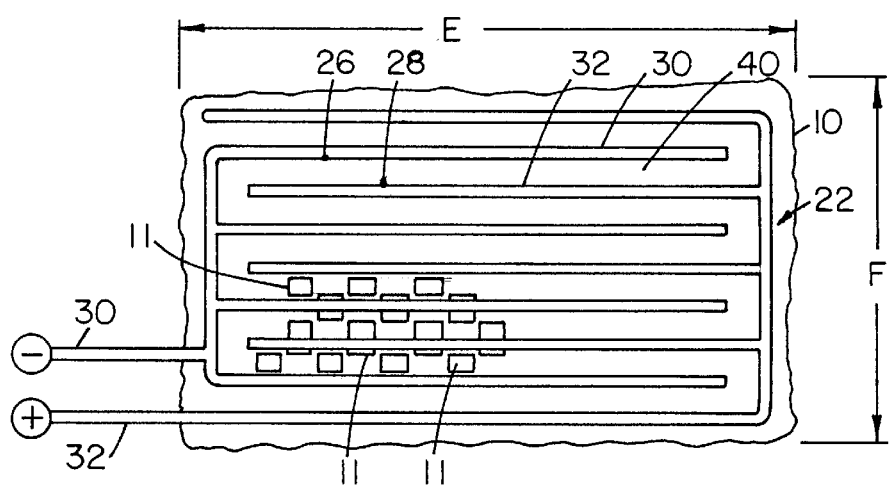
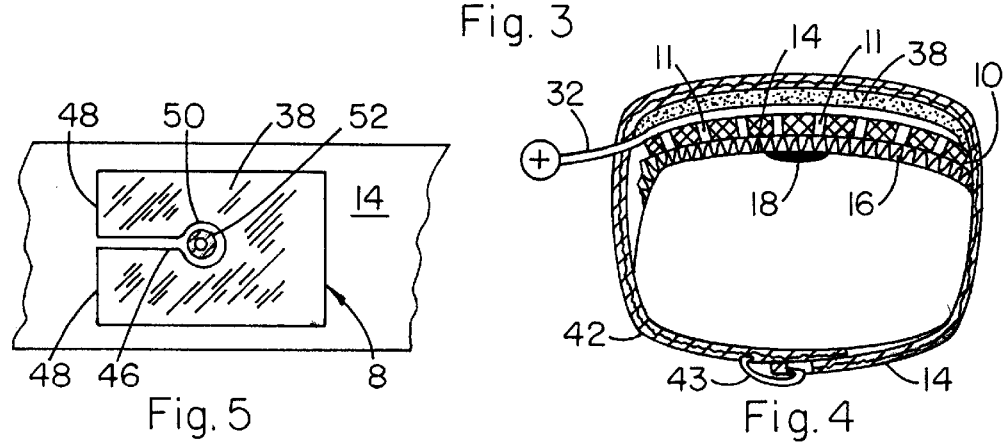

MEDICAL ALARM SYSTEM

BACKGROUND OF THE INVENTION

1. Field

This invention concerns medical alarm systems and particularly systems which can quickly detect and warn the patient himself, the medical staff, or other attendants who may be caring for the patient, e.g., at home or in a hospital, of unexpected excessive or heavy bleeding such as can occur when a wound or incision reopens unexpectedly or when a medical device such as an I.V. tube, syringe, catheter or the like is untimely or inadvertently pulled from a patients artery or vein.

2. Prior Art

Applicant is unaware of any prior systems or devices which are designed to function as described above.

SUMMARY OF THE INVENTION

The invention in one of its preferred embodiments is defined as a monitoring and alarm system for detecting excessive or heavy bleeding from medical patients and for alerting medical attendant(s) wherein the system utilizes a relatively thick sheet-like blood porous base element of electrically non-conductive blood porous material having a proximal side adapted for mounting directly on a patients skin or on a blood porous protective gauze or bandage thereon at a site on the patients body where excessive bleeding can occur unexpectedly, the base having a distal side supporting a normally open electrical circuit, electrically actuable alarm means electrically connected into electrical circuit, electrically actuable alarm means electrically connected into the circuit, and electrical switching means for the circuit responsive to contact with blood to close the circuit and actuate the alarm means to alert said medical attendant(s) to said excessive bleeding.

BRIEF DESCRIPTION OF THE DRAWINGS

The invention will be further understood from the drawings and description herein, wherein:

FIG. 1 is a cross-sectional view of one preferred embodiment of the present system positioned on a patients arm over the site of a wound or incision;

FIG. 2 is a view as in FIG. 1 showing a variation in the electrical circuit mounting;

FIG. 3 is a view of one exemplary type of electrical circuit useful in the present invention taken along line 3—3 of FIG. 1 in the direction of the arrows with only a representative number of pores shown in the base means;

FIG. 4 is a cross-sectional view taken along line 4—4 of FIG. 1 in the direction of the arrows and showing a wrap means for attaching the present system to a patients limb or body; and FIG. 5 is a top view of a special shape for the present system.

DETAILED DESCRIPTION OF PREFERRED EMBODIMENTS

Referring to the drawings and with particular reference to the claims hereof, the present system generally designated 8 comprises a relatively thick sheet-like base means 10 of electrically non-conductive, blood porous material having a proximal side 12 adapted for mounting directly on a patients skin 14 or on a porous protective gauze, bandage or other such porous medical item 16 thereon at a site 18 on the patients body where bleeding can occur, said base means having a distal side 20 with a a predesigned distance "d", electrically actuable visual, sound or physical alarm means 24 electrically connected into said circuit means, and electrical switching means comprising any adjacent electrical contact portions anywhere along electrical conductors 30 and 32 such as 26,28 in said circuit means responsive to bridging contact with blood to close said circuit means and actuate said alarm means to alert medical attendant(s) to said excessive bleeding.

The base 10 must be of electrically non-conductive material such as polyolefins, PVC, polyester, urethanes, natural or synthetic rubbers or elastomers, any of which may be plastisols or which preferably are of foamed cellular structure to provide substantial flexibility and softness to the base. The base is preferably configured as a flexible netting type structure having a thickness of from about $1/32$ to about $3/16$ in., and having from about 6 to about 20 pores 11 per inch, most preferably from about 9 to about 16 pores per square inch, and wherein said pores average in area from about 0.002 to about 0.02 $in^2$, most preferably from about 0.005 to about 0.01 $in^2$. The pores can be of any shape including square, rectangular, round or oval. The manufactured dimensions E and F of the system is determined by the area to be monitored and can range, for example, from a square inch to 50 or more square inches.

The essential character of the base is that the pores must allow free flow of blood from the bleed site 18 to bridge the gap between the conductors 30,32 of the circuit 22. The sensitivity of the system to bleeding can, of course, be increased by reducing the values of "d", e.g., by reducing the thickness of the base. This base thickness, while having an allowable wide dimensional range, should not be so thin as to allow normal or expected fluid leakage from the site to easily fill up the pores and bridge the circuit conductors, whether an intermediate barrier such as gauze 16 is used or not.

It is noted that the present system is intended to be placed on the patient such that the blood would have to flow or migrate substantially upwardly against the force of gravity to reach the electrical circuit. Such placement more easily guarantees that casual seepage of blood or other body fluid from site 18 would not trigger the alarm, particularly where an intermediate absorptive element such as 16 is employed.

The electrical circuit 22 in a simple but very efficient form as shown in FIG. 4 consists of side by side conductor 30,32 which may be supported by and held directly on the distal side 20 of the base. These conductors may also be supported on either the proximal 34 or distal side 36 of a support such as 38, or encased by said support. This support, preferably, is highly absorptive of blood and constructed to allow rapid migration of blood throughout the support for bridging a gap such as 40 between the conductors.

The spacing of the conductors should be sufficiently small to allow blood to readily complete the circuit. Spacings of from about 0.1 to about 0.75 in., have been found to operate with great rapidity for a more than small or casual blood flow. In this regard, it is apparent that extremely sensitive switch means employing relays or the like in the circuitry can be employed to operate the alarm on very low electrical sensing or switching current flowing between the conductors. The use of low voltage battery sensing or switching power, e.g., 1–9 volts, is preferable, and, of course, can be relayed into house or hospital wiring, if desired.

The type of alarm is readily selected by one skilled in the art and can be, for example, flashing lights, ringing bell, or even the physical jostling of a chair or the like in which an attendant may be sitting, whether in or out of a hospital setting. An effective sound alarm is the Model BWD-HWA WATCHDOG WATER Alarm marketed by Glentronics, Inc., Glenview, Ill.

Referring to FIG. 4, a wrap means 42 such as an Ace bandage and securement clip 43 or the like may be employed to hold the system to the patients arm, leg, or even torso or other body part. It is noted that the present system, particularly in embodiments where the various elements such as 16, 10, 22 and 38 are pre-assembled as a unit, can be placed in any exterior location on the body such as adjacent any body orifice and operate effectively to detect and alarm for excessive bleeding. In this regard, such a unit can be provided with adhesive material, preferably water insoluble and of adhesive bandage type, around the edges of the base or gauze for convenient attachment to the skin such as at locations 44.

Referring to FIG. 5 the present system 8 is configured with a slot or split 46 which extends from one edge 48 to an inner aperture such as 50 which passes completely thru the system from top to bottom. This aperture can be tailored in size and shape to accommodate a medical item 52 such as an I.V. tube, catheter or the like which is affixed into a patients vascular system.

This invention have been described in detail with particular reference to preferred embodiments thereof, but it will be understood that variations and modifications will be effected within the spirit and scope of the invention.

We claim:

1. A monitoring and alarm system for detecting excessive bleeding from medical patients and for alerting medical attendant(s) thereof, said system comprising a relatively thick sheet-like base means of electrically non-conductive, blood porous material having a proximal side adapted for mounting directly on a patients skin or on a porous protective gauze or bandage thereon at a site on the patients body where heavy bleeding can occur due to inadvertent opening of a wound or incision or due to inadvertent extraction of a syringe, I.V. tube, catheter or other invasive medical implement, said base means having a distal, a normally open electrical circuit means positioned adjacent said distal side and spaced from said proximal side a predesigned distance, electrically actuable visual, sound or physical alarm means electrically connected into said circuit means, and electrical switching means for said circuit means responsive to contact with blood to close said circuit means and actuate said alarm means to alert said medical attendant(s) to said excessive bleeding.

2. The system of claim 1 wherein said circuit means comprises at least two spaced apart electrical conductors positioned adjacent said distal side of said base means, wherein one conductor is connected to a power lead and the other conductor is connected to a ground lead of a power source, and wherein said switching means comprises at least one gap between contact portions of said spaced conductors and adapted to be bridged by electrolytic blood to electrically connect said contact portions.

3. The system of claim 2 wherein said power source is selected from the group selected from battery power, house, clinic or hospital power, or generator power.

4. The system of claim 2 wherein said conductors are mounted on or imbedded in a non-conductive support means having a high capacity for blood absorption and migration.

5. The system of claim 4 wherein said support means is affixed to said distal side of said base means, and wherein said base means is comprised of a flexible netting type structure having a thickness of from about 1/32 to about 3/16 in., and having from about 6 to about 20 pores per square inch, wherein said pores average in area from about 0.002 to about 0.02 $in^2$.

6. The system of claim 5 wherein the material of said netting is comprised substantially of a material of the group consisting of polyolefin, PVC, polyester, polyurethane, or natural or synthetic rubber or elastomers.

7. The system of claim 4 wherein the material of said support means comprises a mat of natural fibers.

8. The system of claim 4 wherein the material of said support means comprises a mat of felt.

9. The system of claim 4 wherein the material of said support means comprises a mat of blood absorptive paper.

10. The system of claim 4 wherein the material of said support means comprises a mat of blotter paper.

11. The system of claim 4 wherein said support means is physically attached to said base means by electrically non-conductive connector means.

12. The system of claim 1 wherein the material of said base means is substantially blood non-absorptive.

13. The system of claim 11 wherein wrap means is provided on said support means for making quick and stable attachment of said system to a patients body.

14. The system of claim 13 wherein the material of said base means is substantially blood non-absorptive.

15. The system of claim 11 wherein a layer of blood absorbing medical gauze is affixed to the proximal side of said base means to thereby provide a unitary bandaging and bleeding alarm unit.

16. The system of claim 15 wherein wrap means is provided on said support means for making quick and stable attachment of said system to a patients body.

\* \* \* \* \*